(12) United States Patent
Marbach et al.

(10) Patent No.: US 9,261,404 B2
(45) Date of Patent: Feb. 16, 2016

(54) APPARATUS FOR TESTING SAMPLES USING RAMAN RADIATION

(71) Applicant: GLAXO GROUP LIMITED, Brentford, Middlesex (GB)

(72) Inventors: Ralf Marbach, Oulu (FI); Jussi Tenhunen, Oulu (FI)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/365,699

(22) PCT Filed: Dec. 12, 2012

(86) PCT No.: PCT/EP2012/075137
§ 371 (c)(1),
(2) Date: Jun. 16, 2014

(87) PCT Pub. No.: WO2013/087656
PCT Pub. Date: Jun. 20, 2013

(65) Prior Publication Data
US 2014/0354989 A1    Dec. 4, 2014

(30) Foreign Application Priority Data

Dec. 16, 2011 (GB) .................................. 1121723.9
Apr. 30, 2012 (GB) .................................. 1207452.2

(51) Int. Cl.
*G01J 3/44* (2006.01)
*G01N 21/65* (2006.01)
*G01N 21/03* (2006.01)

(52) U.S. Cl.
CPC ................ *G01J 3/4412* (2013.01); *G01N 21/65* (2013.01); *G01N 2021/0339* (2013.01); *G01N 2021/651* (2013.01)

(58) Field of Classification Search
CPC ................ G01N 21/65; G01N 21/658; G01N 2021/656; G01J 3/44; G01J 3/02
USPC .......................................................... 356/301
See application file for complete search history.

(56) References Cited

U.S. PATENT DOCUMENTS

2009/0244533 A1    10/2009    Matousek et al.

FOREIGN PATENT DOCUMENTS

GB            2259767 A        3/1993

OTHER PUBLICATIONS

Sviridov, et al. "Optical characteristics of cartilage at a wavelength of 1560 nm and their dynamic behavior under laser heating conditions" Journal of Biomedical Optics; 2010; vol. 15, No. 5; pp. 055003-1-055003-8.

*Primary Examiner* — Tarifur Chowdhury
*Assistant Examiner* — Md Rahman
(74) *Attorney, Agent, or Firm* — Dwight S. Walker

(57) ABSTRACT

An apparatus and method using the apparatus for measuring target samples, particularly pharmaceutical products using Raman radiation. The sample is located in an aperture in a wall structure with a reflective surface on one or both of the sides of the wall structure facing respectively the excitation radiation transmitter or the Raman radiation detector. Preferably two reflective surfaces each in hemispherical shape and facing each other in a spherical arrangement are provided, with the wall structure across the diameter of the sphere.

11 Claims, 7 Drawing Sheets

APPARATUS FOR TESTING SAMPLES USING RAMAN RADIATION

CROSS-REFERENCE TO RELATED APPLICATIONS

This application is filed pursuant to 35 U.S.C. §371 as a United States National Phase Application of International Application No. PCT/EP2012/075137 filed 12 Dec. 2012 which claims priority from GB1121723.9 filed 16 Dec. 2011 and GB1207452.2 filed 30 Apr. 2012.

This invention relates to an apparatus for testing of samples, in particular samples of pharmaceutical products, using Raman radiation, and to a testing method using this apparatus.

When exciting photons are directed at a target object, photons are scattered from atoms or molecules of the target object. Most of the scattering events are elastic such that a scattered photon has the same energy or frequency as the exciting photon. This elastic scattering process is called Rayleigh scattering.

Raman radiation results from inelastic scattering of light. When monochromatic excitation radiation is directed to a target material, low-energy modes, such as vibration and rotation of molecules cause small deviations in the wavelength of the monochromatic radiation. The Raman effect is based on such inelastic scattering of photons where a scattered photon has either higher or usually lower energy (Stokes scattering) than the excitation photon as a result of simultaneous change in the vibrational, rotational or electronic quantum state of the molecule or atom. Most of the applications of the Raman effect are involved with the vibrational transitions of molecules. This scattered radiation ("Raman radiation") can be detected by suitable instruments, and as each such deviation is characteristic to each molecule in the material, molecules in the material can thereby be identified.

Spectroscopic techniques and apparatus, for example US-A-2010/0309463 and WO-A-97/22872 relating respectively to a cylindrical cell for scattered light spectroscopy, and an annular scanning trace Raman spectroscopy system are known for use in analysis of samples. WO-A-2007/060467 relates to a scanning system using laser Raman for detection of substances in samples, primarily intended for security scanning for example drugs and explosives.

Compared to other vibrational spectroscopic techniques, a measurement of Raman radiation combines the easy sampling characteristic of a measurement in near infrared (NIR) with the high spectral information content characteristic of measurement in mid infrared (MIR). However, issues restricting the use of Raman spectroscopy are higher cost, excitation of fluorescence, and low sensitivity requiring long integration times being a consequence of the low probability of Raman scattering compared to Rayleigh scattering. The resulting low intensity of Raman emission especially limits the applicability of Raman spectroscopy for process applications where a short integration time is needed.

The required integration time of the Raman system may be defined by two factors: a signal-to-noise ratio (based on the response of the measured target analyte); and signal noise. In many cases, the signal noise is dominated by photon shot noise. If the photon noise is dominated either by Raman photon shot noise or fluorescence photon shot noise, the instrument needs to collect a certain number of photons to reach a certain signal-to-noise ratio. Thus, for two similar measurement systems of Raman radiation having different rates in their collected photons (1/(s*pixel)) or (pixel of the CCD) or (1/(s*1/cm)) (1/cm being the unit of wavenumber), the measurement system having the higher rate produces the required signal-to-noise ratio faster than the slower one, and consequently also provides the desired prediction accuracy more quickly. The fast online measurement system based on Raman radiation may be optimised to provide the maximal rate of detected photons (1/(s*pixel)).

The main components of Raman spectroscopy systems such as lasers, charge-coupled-devices etc. are known and are commercially/practically available. The optics of a Raman system may be divided into four main parts; the excitation, sampling, pickup and spectrograph optics. For simplicity it may be assumed that the pickup is designed to have the same etendue (solid angle area) as a spectrograph.

A Raman system to be applied for online use may be optimised with respect to two properties. First, since excitation lasers are expensive components and the power levels of suitable, commercially available lasers are limited, an optimal system may to be maximised for the efficiency of generated Raman scattering with available excitation power. Secondly, since the price of the spectrograph system increases with its throughput and since the sizes of the available charge-coupled-devices set a limit for the size of the optical etendue of the pickup that can be utilised in at the spectrograph, the instrument geometry may be optimised to provide maximal spectral radiance (photons/(s*mm2*str) of the scattered Raman radiation entering the pickup optics of a receiver.

In transmission Raman spectroscopy, by placing the excitation and pickup on different sides of the sample, typically on the opposite sides of the sample, a predicted Raman spectrum correlates well with a spatially averaged value of a true concentration of a sample over the path between excitation and pickup sides. A measurement in this way is suitable for analysis of powders, tablets or other diffuse and turbid samples.

Raman radiation can be very difficult to measure since its intensity with respect to the excitation radiation is very low, and since it arrives at the detector almost simultaneously with the excitation radiation. Additionally, the excitation radiation can cause fluorescent radiation simultaneously with the Raman radiation.

Various kinds of spectrometers have been used to measure Raman radiation. Owing to the low intensity, an important feature of the measurement is collecting as much radiation energy as possible from a sample for the measurement while on the other hand efficiently filtering out the excitation radiation.

In transmission Raman spectroscopy, a bandpass filter may be used in the proximity of the sample on the front side with respect to the incoming direction of excitation radiation, which is typically a collimated laser beam. The laser beam propagates through the filter but the Raman radiation which scatters back is reflected back to the sample from the bandpass filter, which increases the strength of the Raman radiation on the detecting side. However, both the Raman radiation and the laser beam are typically scattered over a wide solid angle on the detecting side, and only a fraction of the scattered light can be collected to a detector. Additionally, a bandpass filter can be difficult to use near the sample, because the shape of the filter needs to match the shape of the sample, and the filter may receive optically disadvantageous scratches owing to contact with samples. A filter for general use could be placed further from the sample, but this could result in a loss of optical gain.

Various systems for enhancing the collection of Raman radiation are known. U.S. Pat. No. 4,645,340 discloses the use of an optically reflecting spherical surface for efficient collection of Raman scattered light. A sample is placed in the center of an internally reflective spherical surface. A beam of excitation radiation is directed to the sample through an aperture in the sphere. At a right angle from the direction of the excitation beam, the sphere has another aperture through which the scattered light can propagate to a detector. The inner surface of the sphere reflects light directed radially outwards from the sample back to the sample. Hence, light is in principle repeatedly bounced back and forth between the inner surface of the sphere and the sample until it passes through the exit aperture to the detector.

However, there are problems with this known solution. The repeated reflections between the sample and the inner surface of the reflecting spherical surface heavily bias the Raman radiation to the outer surface of the sample, and the interior of the sample remains unmeasured. Hence, a need exists for a better apparatus and method of measurement of Raman radiation.

An object of the present invention is to provide an improved solution to the problems of detecting and measuring Raman radiation, in particular to increasing the number of detected photons from a sample.

According to the present invention, there is provided an apparatus for measuring Raman radiation scattered from a target sample exposed to excitation radiation, characterized in that the apparatus comprises:

a wall structure optically non-transparent to excitation radiation and having an optically transparent aperture therein, configured to have a sample located within or adjacent to said aperture during measurement of Raman radiation, the wall structure being located between a transmitter of excitation radiation and a receiver for Raman radiation;

and an optically reflecting surface facing the wall structure, the reflective surface being configured to reflect optical radiation scattered from the sample back to the sample for enhancing Raman radiation at the receiver.

The excitation radiation may for example be optical radiation, i.e. light, and the source of the excitation radiation may be a laser. Optical radiation may be defined to occupy a band from about 50 nm to about 500 μm. Lasers are commonly used as a source of excitation radiation in Raman spectroscopy. The transmitter is preferably a laser. Fluoresence from the sample can be a cause of interference. Fluoresence decreases with longer wavelength excitation radiation, but too long a wavelength can result in decreased quantum efficiency. A laser emitting excitation radiation of 785 nm was found to be suitable, but 830 nm was better. A laser wavelength range 700-900 nm therefore appears to be preferable.

In the apparatus of this invention the wall structure may be made of any convenient material that is non-transparent to the excitation radiation. If laser excitation radiation is used the wall structure should be of a material that is not likely to be damaged by such intense radiation. For example metal may be a suitable material for the wall structure. The wall structure is preferably specularly reflective (i.e. mirror-like). Alternatively and less effectively the wall structure may be diffuse reflective. The wall structure may be non-reflecting. Reflection from the wall structure may become important since a part of the radiation hitting the reflecting surface(s) will be reflected back toward the wall structure, which may then reflect it back toward the reflecting surface(s).

The optically transparent aperture in the wall structure may for example be a simple opening in the wall structure, of a suitable size and shape to accommodate a sample. For example such an opening may have approximately the same cross-section as a sample being a pharmaceutical tablet. Preferably the edges of the aperture through the wall structure are made reflective, especially specularly reflective. The area of the aperture should be maximized to maximize the energy throughput through a sample in the aperture, but should be small enough as to minimize leakage of radiation scattered from the surface of the sample into any void space between the sample and the wall structure. For example the aperture may incorporate a collar overlapping the edge of the sample to prevent such leakage.

In a preferred embodiment the wall structure has a thickness "t", greater than the thickness of the sample, between its opposed surfaces on the transmitter and receiver sides, and the aperture passes completely through the wall structure from one surface to the other. In such a construction the thickness "t" is such that when the sample is in place in the aperture the surface of the sample is below one or both of the opposite surfaces of the wall structure. In such a construction the aperture is in effect a tunnel between the two opposite surfaces of the wall structure. The sides of the aperture, i.e. the side wall of such a tunnel are preferably also reflective, preferably specularly reflective. Such a construction facilitates adaptation of the system to samples of different thicknesses.

In the apparatus of the invention there may be a reflecting surface only on one side of the wall structure. Preferably there is a reflecting surface on both sides of the wall structure.

The reflecting surface can have various profiles, for example planar, but in a preferred embodiment the reflecting surface is concave. It is well known that concave curved reflecting surfaces have a focal length, and a focal point being a point at which the concave reflecting surface will concentrate radiation reflected from it.

In this embodiment such a concave surface may have a predefined radius of curvature, and this radius may be at least approximately the same as the distance between the aperture in the wall structure and the concave surface on the side of the wall structure that faces the convex surface.

When facing each other with the wall structure between them two such concave curved reflecting surfaces may have a common focal point. The optically transparent aperture is preferably configured to be as close as possible to this common focal point of both concave surfaces. For example the common focal point may be within the aperture.

An embodiment of a concave surface is a spherically curved surface, for example a hemisphere, which term includes a surface as close to a hemisphere as in practice is feasible. In practice ca. 93-98% of an ideal hemisphere appears to be possible. For example a reflecting surface may be configured to cover a major part of a hemisphere on a side of the wall structure, preferably with the aperture located as close as practical to the spherical centre of the hemisphere.

A hemispherical reflective surface has the effect that radiation emitted from an origin at a point at the spherical centre is reflected back from the reflective surface to the origin. Excitation radiation reflected from the surface of a sample at such a centre is consequently reflected back to the sample at that centre. A hemispherical reflecting surface also has the effect of maximizing the solid angle over which emitted radiation can be collected, consequently maximizing gain. With a hemisphere the theoretical maximum solid angle is 90°, but because of practical limitations of equipment 85° appears to be the maximum easily achievable in practice. It is found that the more accurately a sample can be located at such a centre, the more loss of radiation can be minimized.

In the embodiment mentioned above in which the wall structure has a thickness "t" greater than the thickness of the target sample between its opposed surfaces on the transmitter and receiver sides and the aperture passes completely through the wall structure from one surface to the other, and the thickness "t" is such that the surface of the sample when in place in the aperture is below one or both of the opposite surfaces of the wall structure, preferably at least one reflective surface, preferably both reflective surfaces if there is a reflective surface on both sides of the wall structure, are arranged such that the focal point of the reflective surface is at the level of the surface of the wall structure. In such an embodiment if one or both reflective surface is a hemispherical reflective surface then preferably the spherical centre of the one or both hemispherical surface(s) is at the level of the surface of the wall structure. This can have the effects of maximizing the power guided to the sample in the aperture, and of reducing the sensitivity of the gain of the instrument to sample thickness.

Suitably in such an embodiment comprising two hemispherical reflecting surfaces, the wall structure may comprise a wall structure across the equatorial diameter of such a hemisphere such that with a hemispherical reflecting surface on each side of the wall structure, the assembly of reflecting surfaces and wall structure are in the form of a wall across a diameter of a substantially spherical reflecting surface.

In an embodiment of the apparatus of the invention the reflecting surface comprises a first concave surface and second concave surface; the first concave surface and the second concave surface being configured to face each other with an optical axis between them, and to have a distance of their combined focal lengths along the optical axes between them; the wall structure being between the concave surfaces and configured to optically isolate the concave surfaces from each other; the first concave surface comprising an input aperture for transmission of excitation radiation to the sample; and the second concave surface comprising an output aperture for the Raman radiation produced by the interaction between the sample and the excitation radiation, the second concave surface being configured to reflect back to the sample optical radiation passed through or reflected from the sample without hitting the output aperture.

In another embodiment of the apparatus of the invention the reflecting surface comprises a first hemispherical concave surface and a second hemispherical concave surface; the first concave surface and the second concave surface being configured to face each other with an optical axis between them, and to have a distance of at least their combined hemispherical radii along the optical axes between them; the wall structure being between the concave surfaces and configured to optically isolate the concave surfaces from each other; the first concave surface comprising an input aperture for transmission of excitation radiation to the sample; and the second concave surface comprising an output aperture for the Raman radiation produced by the interaction between the sample and the excitation radiation, the second concave surface being configured to reflect back to the sample optical radiation passed through or reflected from the sample without hitting the output aperture.

Various other types of reflecting surface or surfaces may be used.

For example a reflecting surface may comprise at least one retroreflector.

For example a concave curved reflecting surface may comprise a paraboloid at least on one side of the wall structure, for example two paraboloids one on each side of the wall structure.

For example a reflecting surface may comprise a plurality of plane surfaces, each of which being at least approximately parallel with a tangential plane of a corresponding continuous reflecting surface. Such a surface may comprise a polyhedral profile of the concave reflecting surface, comprising a plurality of plane surfaces each of which is at least approximately parallel with a tangential plane of a corresponding continuous concave surface. This construction of reflecting surface may not have a good gain if only a few plane surfaces are used. The optical collecting effect increases with an increasing number of such plane surfaces in the concave polyhedral profile. When the number of plane surfaces is so large that the size of the plane surface is about the same as or smaller than the sample or the aperture in the wall structure, increasing the number of plane surfaces may not lead to further improvement in gain, and the result may not essentially differ from that of a continuously curved surface.

In another embodiment a concave reflecting surface may be a paraboloid, and for example two such paraboloids may be arranged one on each side of the wall structure.

Preferably in the apparatus of the invention the, or one or both reflecting surface(s) are configured to provide specular (mirror-like) reflection, as specularly reflective surfaces are found to minimize radiation losses. Alternatively the, or if there are two, one or both reflecting surface(s) may be configured to reflect diffusely. In diffuse reflection, an incident beam of light is back-scattered from an object at a wide solid angle.

Reflective surfaces may be provided by a layer of reflective metal. Such a layer is preferably provided on the side of the reflective surface which faces the sample. Such metal layers can be vulnerable to damage, so alternately the reflective surface may be provided by a transparent material, e.g. glass, having such a reflective metal on the side facing away from the sample.

The optical axis along the direction of the excitation radiation from the transmitter to the aperture in the wall structure, and the optical axis from the aperture in the wall structure to the receiver are preferably at an angle to each other of ($\alpha$) the absolute value of the sine function of which is larger than zero but is smaller than one.

If the angle ($\alpha$) is too small the excitation radiation may disadvantageously be aligned too directly with the receiver. If the angle ($\alpha$) is too large, e.g. 45° there is a possibility of collection of stray photons being collected from the from the wall structure rather than from the sample leading to reduced accuracy and lower signal levels. An angle ($\alpha$) in the range 10-20° appears to be suitable.

The apparatus of this invention facilitates the high speed measurement, e.g. screening of samples using Raman spectroscopy. In particular the apparatus is suited for the measurement, e.g. screening and testing of multiple products produced in a production line for the presence and/or quantity of specific substances in the products. Such substances may be desired ingredients of such products, or undesired ingredients of the products. An example of such products is pharmaceutical products such as tablets and pills, in which a desired ingredient is an active pharmaceutical substance, and an undesired ingredient is an impurity. The apparatus of the invention can therefore facilitate the high speed screening and testing of such pharmaceutical products.

In a further aspect the present invention provides a system for testing target samples on the basis of Raman radiation scattered from a target sample, comprising an apparatus as described herein provided with a mechanism configured to move a target sample into or adjacent to the aperture of said apparatus for a time period long enough to enable the apparatus to measure Raman radiation scattered from the target sample, and thereafter to move the target sample away from the aperture.

The mechanism may be configured to pick separate samples one by one and to move them one by one for measurement in or adjacent to the aperture of the wall structure. Alternatively the mechanism may be configured to deliver a continuous stream of samples, e.g. as provided by a conveyor, for measurement in or adjacent to the aperture of the wall structure. A mechanism, suitably the same mechanism as delivers the samples for measurement, may also remove the samples from the aperture after the sample has been measured.

Suitable mechanisms will be apparent to those skilled in the art, for example pick-and-place robots, conveyors etc.

In a further aspect the present invention provides a method of measuring samples on the basis of Raman radiation comprising directing excitation radiation at a sample located within or adjacent to an optically transparent aperture in a wall structure optically non-transparent to the excitation radiation, the wall structure being located between a transmitter of excitation radiation and a receiver for Raman radiation;

and reflecting scattered radiation from the sample back to the sample from a reflecting surface facing the wall structure for enhancing Raman radiation at the receiver.

Suitable and preferred apparatus for this method are as described herein.

Suitable and preferred embodiments of the method of this aspect of the invention are analogous to the suitable and preferred features of the apparatus described herein.

For example radiation scattered from the sample may be reflected back to the sample by a reflecting surface on only one side of the wall structure, or alternately radiation scattered from the sample may be reflected back to the sample by a reflecting surface on both sides of the wall structure.

For example radiation scattered from the sample may be reflected back to the sample by a concave reflecting surface.

For example the method may comprise directing an excitation beam from an input aperture in a first concave reflecting surface to a sample in an optically transparent aperture in a wall structure whereby the radiation scattered from the sample is reflected from the sample back to the sample by the first concave surface; allowing optical radiation to pass through the optically transparent aperture together with the sample; reflecting radiation passed through or reflected from the sample without hitting the output aperture back to the sample by a second concave surface; outputting the Raman radiation formed on the interaction between the sample and the excitation beam on its way through the sample to a detector via an output aperture in the second concave surface.

In this method the direction of the output radiation may be in a direction along an optical axis from the aperture in the wall structure to the output aperture which differs by an angle ($\alpha$), the absolute value of the sine function of which is larger than zero but is smaller than one, from the optical axis from the input aperture to the aperture in the wall structure.

In the method each of such concave surfaces may have a predefined radius of curvature and the radius being at least approximately the same as the distance between the estimated position of the sample in the aperture in the wall structure and the concave surface on the side of the wall structure facing the reflecting surface.

In the method the reflecting surface may comprises at least one retroreflector, or the reflecting surfaces may comprise two paraboloids at least one on side of the wall structure.

In the method the, or one or both of the reflecting surfaces may reflector provide specular reflection.

In the method both reflecting surfaces may cover a major part of a hemisphere on each side of the wall structure.

In the method a reflecting surface may comprise a plurality of plane surfaces, each of the plane surfaces being at least approximately parallel with a tangential plane of a corresponding continuous reflecting surface.

The method may comprise moving separate samples one by one to the aperture of the wall structure for the measurement, then moving each sample away from the aperture after the measurement. In a preferred embodiment the method may comprise measuring a continuous stream of samples.

The apparatus and method of this invention is particularly suited for measuring a pharmaceutical sample, for example a pharmaceutical sample which has a solid surface, such as tablets and pills. The dimensions of such tablet will of course be a determining factor in the dimensions and other features of the apparatus. For example a larger sample size will require larger reflective surfaces, and with increasing sample thickness the Raman signal may become fainter and may need a longer integration time.

The present apparatus and method can also be applied for measuring a liquid sample, for example by causing the liquid sample to flow through a tube which is transparent to the excitation and scattered radiation in the vicinity of the aperture in the wall structure.

In the measurement described herein optical radiation propagates through the target sample, e.g. a pharmaceutical sample at least mainly via a diffusion process, which means that optical radiation is strongly scattered in the sample. The target sample may be still or move when measured. The state of the inner material of the target sample may be solid or liquid, including a gel-like state. A pharmaceutical sample may be a tape, tablet, pill or a capsule (provided the capsule shell is transparent to the excitation and scattered radiation). Pharmaceutical samples are usually a mixture of several substances pressed into a tablet or enclosed inside a capsule. For example the sample may be a pharmaceutical product from a production line and the method of the invention may be a measurement to assess quality, e.g. the purity or the presence of impurities, upon the basis of which assessment the sample may be either further processed or disposed of. The method of this invention appears to be suitable for all kinds of samples, but usually pharmaceutical samples are white, near white, turbid or diffuse in colour.

The apparatus and method of this invention provide several advantages. The Raman scattering efficiency based on Raman scattered photons/excitation photons is increased. Raman radiation is collected effectively. The intensity of the Raman scattered signal observed by the receiver is increased, for example by a factor of two or much more.

The invention will now be described in greater detail by means of examples of preferred embodiments and with reference to the attached drawings, in which some embodiments are shown. The present invention may be embodied in many different forms and should not be construed as limited to the embodiments set forth herein. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
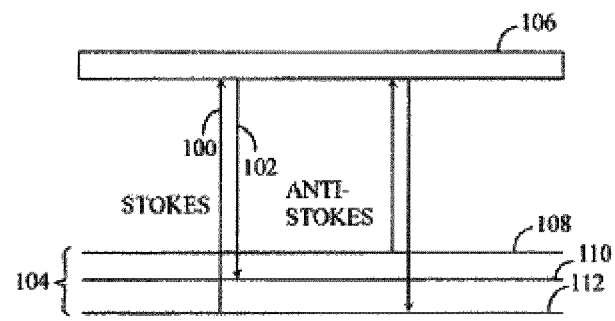
FIG. 1 shows interaction between matter and optical radiation.

Referring to FIG. 1, this shows interaction between optical radiation and matter in a simplified form. Optical radiation may be defined to occupy a band from about 50 nm to about 500 µm. In absorption of a photon, total molecular energy jumps from a base energy level 104 to an excited energy level 106. When the total molecular energy returns from the excited level 106 to the base level 104, often a photon is emitted. Because of the vibrational and/or rotational modes of molecules, for example, a base energy level 104 may actually have several sub-levels 108, 110, 112 and in Raman scattering the total molecular energy may return to a sub-level 108, 110, 112 different from the base level 104 it jumped from. When absorption 100 has energy higher than that of emission 102, the emitted Raman radiation is based on Stokes scattering, and when the energies of absorption 100 and emission 102 are vice versa, the emitted Raman radiation is based on anti-Stokes scattering. When a spectrum of a sample is measured, wavelengths of emitted Raman radiation 102 provide means for identifying a desired molecule in the sample. Additionally, the proportion of the desired molecule in the sample may also be determined. In a pharmaceutical sample for example the quantity of at least one desirable ingredient may for example be determined.

Figure 2A:
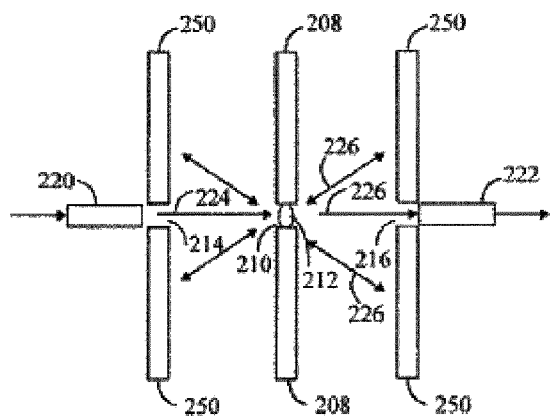
FIG. 2A shows a measuring device with reflecting surfaces on both sides of the wall structure.

FIG. 2A illustrates a principle of a measuring device for transmission Raman spectroscopy. In the illustrated embodiment, an optically non-transparent wall structure 208 comprises an optically transparent aperture 210, e.g. a simple opening through the wall structure 208 in which can be placed a sample 212 for measurement. A transmitter 220 of excitation radiation and a receiver 222 of the optical radiation from the sample 212 are on different sides of the wall structure 208. The transmitter 220 may for example be a laser. The receiver 222 may for example be a spectrometer. The laser may be a spectrally narrow semi-conductor laser, and the spectrometer may have a semi-conductor detector such as a CCD (Charge Coupled Device) for detecting a spectrum of the radiation received from the sample 212.

A reflecting surface 250 faces the wall structure 208. In FIG. 2A a reflecting surface 250 is on both sides of the wall structure 208. The reflecting surface 250 may have a predetermined position with respect to the wall structure 208, with the distance between the position of the sample 212 and the reflecting surface 250 being predetermined. The distance between the surface of the sample 212, where the position of the surface of the sample 212 may be estimated, and the reflecting surface 250 may be predetermined. The reflecting surface 250 reflects optical radiation scattered from the sample 212 back to the sample 212 for increasing Raman radiation at the receiver 222. The inclination angle of the reflecting surface 250 relative to the wall structure 208 may also be predetermined. The inclination angle may depend on the distance of the reflecting surface 250 from the wall structure 208 and on the distance of the wall structure 208 from the transmitter 220 and/or the receiver 222.

The transmitter 220 is shown positioned behind the reflecting surface 250, with an aperture 214 in the surface 250 through which the beam of excitation radiation 224 may pass. In a similar manner the receiver 222 is shown positioned behind the reflecting surface 250 with an aperture 216 in surface 250 through which the beam of excitation radiation 226 may pass. However, the transmitter 220 and/or the receiver 222 may also be at least partly located in apertures 214, 216 of the respective reflecting surfaces 250. The transmitter 220 and/or the receiver 222 may also be at least partly in the space between the wall structure 208 and the respective reflecting surface 250.

Figure 2B:
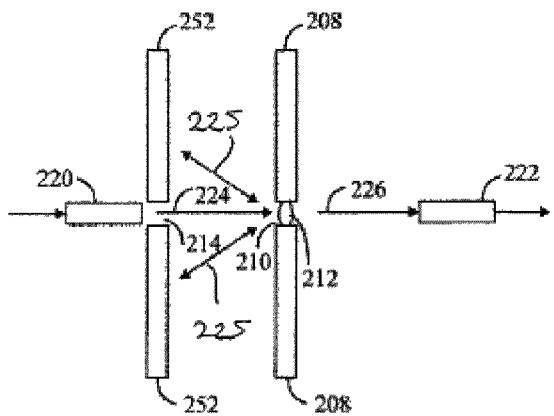
FIG. 2B shows a measuring device with reflecting surfaces on the transmitter side of the wall structure.

FIG. 2B shows a measurement configuration where a first reflecting surface 252 is only on the same side of the wall structure 208 as the transmitter 220.

The first reflecting surface 252 may comprise an input aperture 214. The input aperture 214 may be an opening in the first reflecting surface 252 to direct an excitation beam 224 from the transmitter 220 to the sample 212. Alternatively or additionally, the input aperture 214 may be for an optical element for directing the excitation beam 220 to the sample 212. Such an optical element may be an optical fibre of a pig-tailed transmitter (term of the art referring to an optical source having plural optical leads leading from it) 220. The first reflecting surface 252 reflects the optical radiation 225 reflected from the sample 212 back to the sample 212. The reflections cause the excitation radiation and the Raman radiation to diffuse through the sample 212. No radiation can pass through the wall structure 208 to the other side and hence the wall structure 208 maximally lowers the strength of excitation radiation, particularly the part which is scattered, in detection. Additionally, since the wall structure 208 and the aperture 210 cause all optical radiation which is to be detected to pass through the sample 212, the effect of the interior of the sample 212 on the excitation radiation is enhanced in the measurement of the Raman radiation.

Figure 2C:
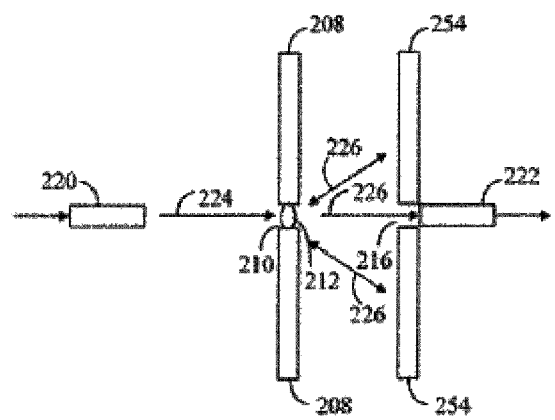
FIG. 2C shows a measuring device with reflecting surfaces on the receiver side of the wall structure.

FIG. 2C shows a measurement configuration where a second reflecting surface 254 of the reflecting surface 250 is only on the same side of the wall structure 208 as the receiver 222.

The second reflecting surface 254 in FIG. 2C may comprise an output aperture 216. The output aperture 216 may be an opening in the second reflecting surface 254 for letting the optical radiation 226 from the sample 212 propagate to the receiver 222. Alternatively or additionally, the output aperture 216 may be for an optical element directing or leading optical radiation to a slit of a spectrometer of the receiver 222. Such an optical element may be an optical fibre of a pig-tailed receiver 222, for example a fibre directing the optical radiation 226 to the receiver 222. The optical radiation 226 from the sample 212 comprises the Raman radiation formed on the interaction between the sample 212 and the excitation beam 224 scattered by the sample 212. The second reflecting surface 254 reflects the optical radiation 226 which has passed through or reflected from the sample 212 and which has not found a way to the receiver 222 back to the sample 212. After a plurality of reflections, a large part of the optical radiation is consequently fed to the output aperture 216 and consequently to detector 222.

When the reflectivity R of the sample 212 is high, for example 90% or higher, most of the excitation radiation is reflected from the sample 212. The first reflecting surface 252 returns the reflected excitation radiation back to the sample 212. Since a series of reflections takes place, the net gain G of reflections may be expressed as a geometrical series:

$G=1/(1-q)$ where q is $R*(\Omega/\pi)*rs$, $\Omega$ is a solid angle of the first reflecting surface 252 observed from the position of the sample 212 in the aperture 210 in the wall structure 208, $\pi$ is a constant about 3.1415926, and rs is the reflectivity of the first reflecting surface 252. If it is assumed that q is 0.75, the gain is 4, which means that the first reflecting surface 252 can apply a four times larger amount of optical radiation to the surface of the sample 212 than in the case without the first reflecting surface 252. Such a gain makes the effect of the interior of the sample 212 observable in the measurement.

On the other side of the wall structure 208 and the sample 212 a similar series of reflections involving reflecting surface 254 takes place. Since optical radiation can only exit the volume between the second reflecting surface 254 and the wall structure 208 through aperture 216 to the receiver 222 the second reflecting surface 254 substantially increases the optical radiation including Raman radiation directed to the receiver 222.

Together in combination as shown in FIG. 2A the first and the second reflecting surfaces 252, 254 on opposite sides of the wall structure 208 increase the strength of the Raman radiation that can be detected by the receiver 222.

In an embodiment, either or both of the reflecting surfaces 252, 254 may reflect diffusely. In diffuse reflection, an incident beam of light is back-scattered from an object at a wide solid angle. In an embodiment, the wall structure 208 may also reflect diffusely. When the reflecting surfaces 252, 254 provide a diffuse reflection the reflectance of the wall structure 208 may become important since a part of the optical radiation hitting the diffuse reflecting surfaces 252, 254 is directed towards the wall structure 208. In order to collect the optical radiation from the wall structure 208, it may be diffusely reflected back towards either the first reflecting surface 252 or the second reflecting surface 254, depending on which side of the wall structure 208 the reflecting surface 252, 254 is located.

In an embodiment based on diffuse reflecting first and the second reflecting surfaces 252, 254 the basic idea is the same as with an embodiment based on specular reflecting surfaces. The first reflecting surface 252 returns the optical power reflected from the sample 212 back to the sample 212 until it penetrates the surface of the sample 212 or is absorbed. However, diffuse reflections from the first reflecting surface 252 make a part of the optical radiation take more (randomly or nearly randomly directed) reflections than in the embodiment based on specular reflections before the penetration. On the other side of the wall structure 208, diffuse reflections from the second reflecting surface 254 make a part of the optical radiation take more reflections than in the embodiment based on specular reflections before finding its way to the receiver 222.

Figure 3A:
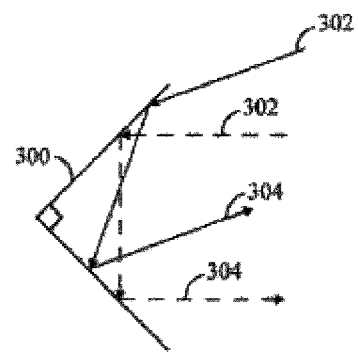
FIG. 3A shows a retroreflector.

FIG. 3A shows a cross section of a retroreflector 300. A beam 302 of optical radiation directed to the retroreflector 300 is reflected back parallel to its incoming direction 304 irrespective of the angle of incidence beam 302. A retroreflector may be formed by three reflecting planes at 90° angles to each other, i.e. a so-called "cube corner". The reflecting surface 250 may comprise at least one such retroreflector 300.

Figure 3B:
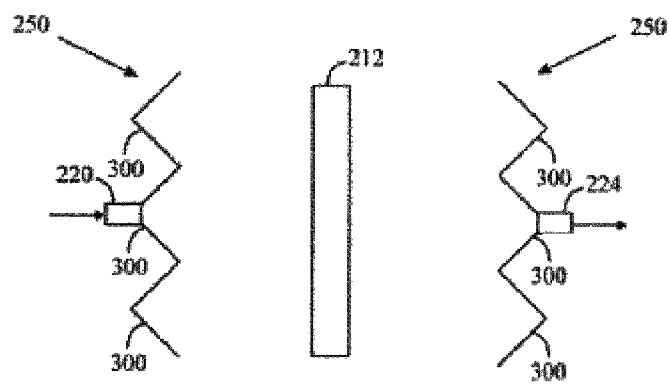
FIG. 3B shows retroreflectors on each side of the wall structure.

FIG. 3B presents an embodiment comprising two reflecting surfaces 250 located on opposite sides of a sample 212 in a wall structure (not shown) utilizing a plurality of retroreflectors 300.

Figure 3C:
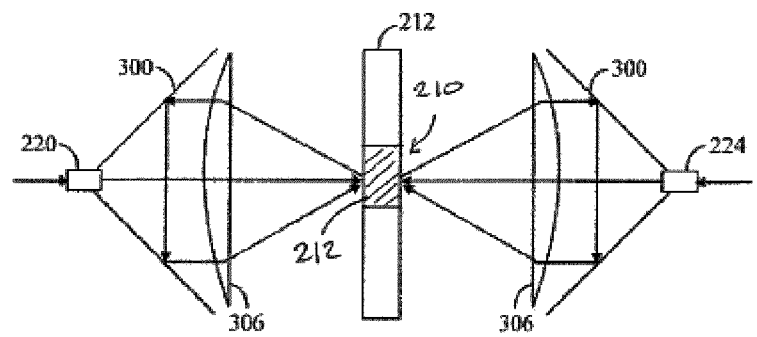
FIG. 3C shows a retroreflector on each side of the wall structure.

FIG. 3C presents an embodiment where the reflecting surface comprises a retroreflector 300. The retroreflector 300 may comprise a lens 306 for focusing the reflected optical radiation on the sample 212 onto the transmitter 220 side of the wall structure (not shown). In a corresponding manner, the retroreflector 300 may comprise a lens 306 for focusing the reflected optical radiation onto the sample 212 on the receiver 222 side of the wall structure (not shown). The transmitter 220 and/or the receiver 222 may utilize the lens 306 (as shown in FIG. 3C) or the apertures 214, 216 may penetrate the respective lenses 306 (not shown in FIG. 3C).

Figure 4:
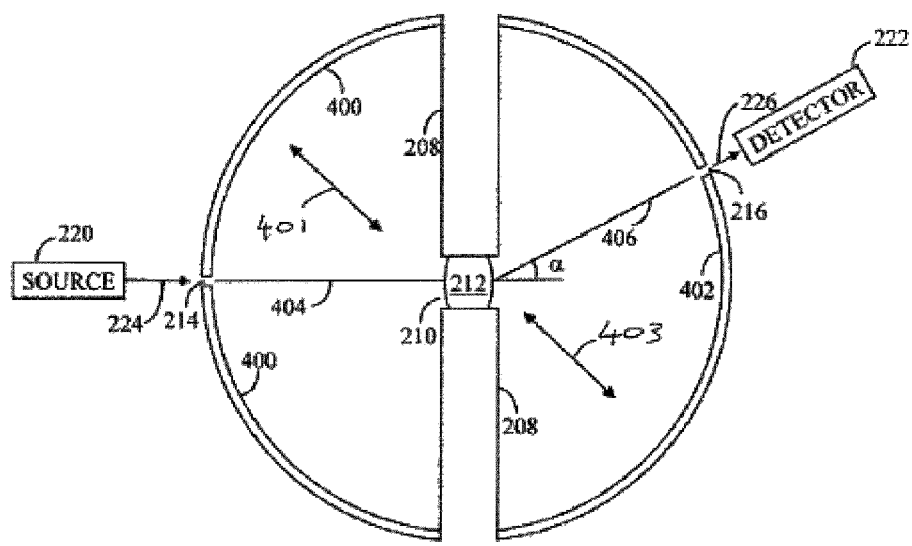
FIG. 4 shows two hemispherical reflecting surfaces facing each other.

FIG. 4 shows two concave reflecting surfaces 400, 402 for measuring Raman radiation, being a first concave reflecting surface 400 and a second concave reflecting surface 402 which face each other. The surfaces 400, 402 may for example be surfaces of glass or metal. The first concave surface 400 has a predefined focal length. The second concave surface 402 also has a predefined focal length which may be the same as or different from that of the first concave surface 400. The curvatures of concave surfaces 400, 402 are close to spherical, and are segments of spheres. The curvatures of surfaces 400, 402 may alternatively be slightly parabolic or ellipsoid. The concave surfaces 400, 402 have centres of curvature at a common point. The distance between the concave surfaces 400, 402 along a first optical axis 404 and a second optical axis 406 is at least approximately the same as the combined focal lengths of the concave surfaces 400, 402. The first optical axis 404 may be considered as a straight line between an input aperture 214 and the aperture 210 of the wall structure 208. The second optical axis 404 may be considered as a straight line between the aperture 210 of the wall structure 208 and an output aperture 416.

The sine function of an angle $\alpha$ between the first optical axis 404 along the excitation beam 224 to the aperture 210 in the wall 208 and the second optical axis 406 from the aperture 210 in the wall 208 towards the receiver 222 has an absolute value larger than zero but smaller than one. Such a value for the angle $\alpha$ indicates that the optical axes 404, 406 on the different sides of the wall structure 208 are not in a straight line. The purpose of the angle $\alpha$, whose absolute value can be considered to actually be between zero and $\pi/2$, is to reduce the strength of the excitation radiation received by the receiver 222.

A wall structure 208 is located between the concave surfaces 400, 402. The purpose of the wall structure 208 is to optically isolate the concave surfaces 400, 402 from each other. The wall structure 208 comprises an optically transparent aperture 210 which is located at least approximately at a common focal point of both concave surfaces 400, 402. The aperture 210 provides a place for the sample 212.

In an embodiment, at least one of the concave surfaces 400, 402 may provide a specular reflection. In specular reflection, an incident beam of optical radiation is reflected as a beam of optical radiation in a direction defined by the law of reflection. Either of both of the specular reflecting concave surfaces 400, 402 may image the surface of the sample 212 back to the surface of the sample 212. When the concave surfaces 400, 402 provide a specular reflection, the optical reflectivity of the wall structure 208 is usually irrelevant to the collecting power of the Raman measurement. However, the wall structure 208 may also be made of a material having a high reflectivity. The wall structure 208 may be diffusely or specular reflective. Alternatively, the wall structure 208 may have a low reflectivity.

In an embodiment, at least one of the concave surfaces 400, 402 may reflect diffusely.

The concave surfaces 400, 402 may be metal mirrors, for example comprising silver, though other reflective metals may also be used. Specular reflection may be achieved by making the surface finish of the concave surfaces 400, 402 highly polished. Diffuse reflection may be achieved by making the concave surface 400, 402 suitably rough.

Each of the concave surfaces 400, 402 may cover a whole hemisphere or a major part of a hemisphere, with the wall structure 208 occupying an equatorial diameter of the sphere formed by the two hemispherical surfaces 400, 402. In an embodiment, each of the concave surfaces 400, 402 has a predefined radius of curvature and the radius is at least approximately the same as the distance between the aperture 210 in the wall structure 208 and the concave surface 400, 402 on that side of the wall structure 208. The centre of radius for both hemispheres may be approximately at the surface of the sample 212.

Figure 5:
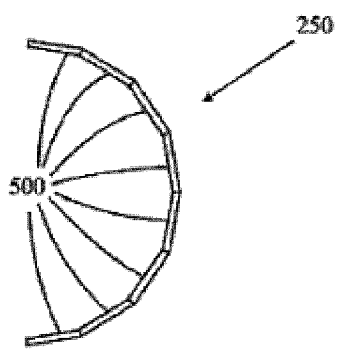
FIG. 5 shows a reflecting surface with a plurality of plane mirrors.

FIG. 5 presents a cross-section of a polyhedral profile of one of the concave reflecting surfaces 250. The surface 250 comprises a plurality of plane surfaces 500, each of which is at least approximately parallel with a tangential plane of a corresponding continuous concave surface. The number of plane surfaces 500 is so large that the size of the plane surface 500 is about the same as or smaller than the sample 212 or the aperture 210 in the wall structure 208.

Figure 6:
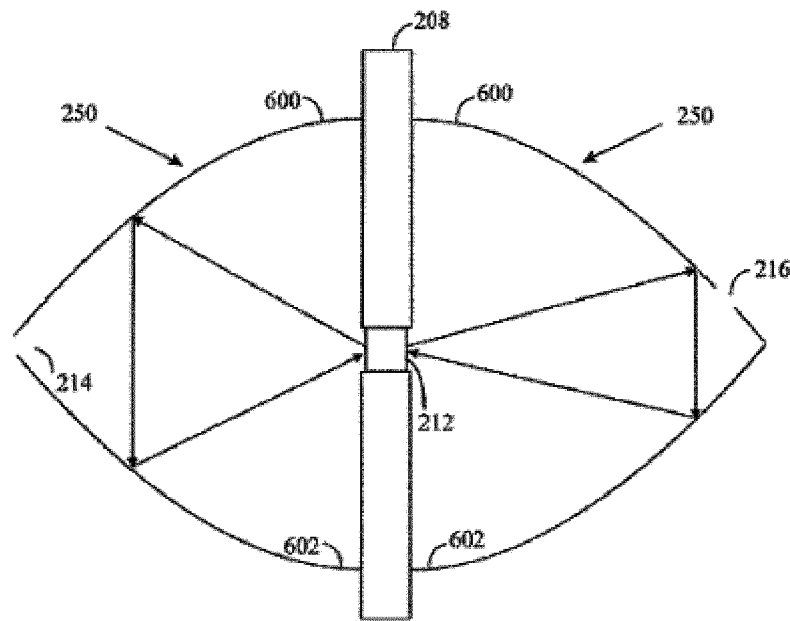
FIG. 6 shows paraboloid surfaces as a reflecting surface.

FIG. 6 presents an embodiment where the reflecting surface 250 comprises two reflecting paraboloids 600, 602 on both sides of the wall structure 208, although only one of such paraboloids 600, 602 may be located only on either side of the wall structure 208. The first paraboloid 600 enables an optical beam passing through aperture 214 and scattered from the sample 212 to be reflected to the second paraboloid 602 which then is able to reflect the optical beam back to the sample 212.

Figure 7:
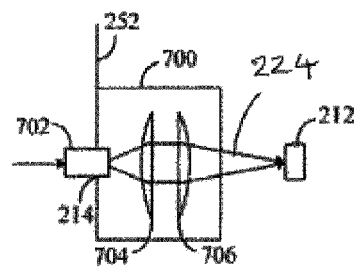
FIG. 7 shows an optical element associated with a transmitter.

FIG. 7 presents an optical element 700 of the excitation side. To focus excitation radiation on the sample 212 a component like the optical element 700 may be needed. A source 702 may be an emitting part of the transmitter 220 shown in previous drawings or an optical fibre coupled to the transmitter 220. The source 702 may be placed in the input aperture 214 of the first reflecting surface 252. The excitation radiation 224 is directed in a solid angle from the source 702 onto the sample 212. The optical element 700 may comprise lenses 704 and 706. The excitation radiation 224 may be collected with the lens 704 which may collimate the excitation radiation. The collimated excitation radiation 224 may be converged or focused on the sample 212 by the second lens 706.

An optical element 700 may also be on the other side of the first reflecting surface 252 than that in FIG. 7. Additionally, a notch filter may be provided to have a narrow band for the excitation beam 224.

Figure 8:
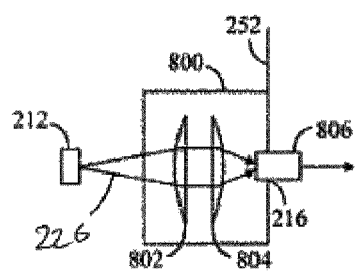
FIG. 8 shows an optical element associated with a receiver.

FIG. 8 shows an optical element 800 of the pickup side. The optical radiation 226 from the sample 212 may be collected in a solid angle characteristic to an optical element 800. A lens 802 inside the optical element 800 may collimate the optical radiation 226. The collimated optical radiation 226 may be converged or focused onto the output aperture 216 by a second lens 804 of the optical element 800. Alternatively, the collimated optical radiation 226 may be converged or focused onto a slit of a spectrometer (not shown) or an optical fibre 806 leading to the spectrometer by a second lens 804. The spectrometer or an optical fibre 806 fully or partly represents the receiver 222. The optical element 800 may also be on the other side of the second reflecting surface 252 than that in FIG. 8. Additionally, a Rayleigh line rejection filter may be placed between the lenses 802, 804 to separate the Raman radiation from the rest of the optical radiation.

A fraction of the optical radiation 226 hitting the optical element 800 may be reflected back to the reflecting surface 252. But since the reflecting surface 252 reflects a large proportion of the optical radiation 226 back to the optical element 800, the efficiency of collecting this part of the optical radiation is high. A corresponding effect takes place on the transmitter's side where the optical radiation 224 is guided efficiently into the sample 212.

In every embodiment, the received optical radiation 226 may be filtered in several manners known by a person skilled in the art in the receiver 222 for effectively detecting the Raman radiation. The filtering may for example include temporal and band pass filtering.

Figure 9:
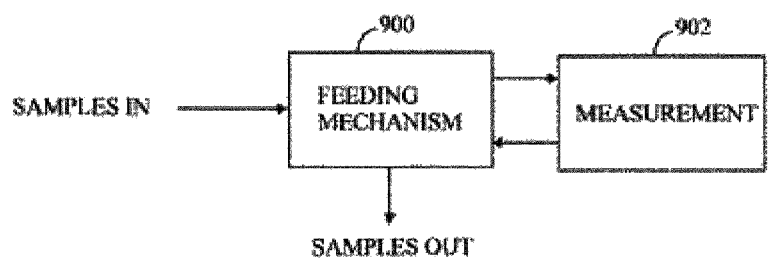
FIG. 9 shows a system feeding samples to the measurement.

FIG. 9 presents a block diagram of an automated machine performing Raman measurements of samples. A flow of samples such as tablets is fed to a mechanism 900 which moves the tablets to a measuring unit 902 comprising the reflective surface(s) as described above and positions the samples in the aperture 210 of the wall structure 208. The mechanism 900 may be a part of the wall structure 208 or the wall structure 208 may be a part of the mechanism 900. Alternatively the mechanism 900 may be structurally independent of the wall structure 208.

The tablets may be fed to the mechanism 900 by a conveyor or the like. The mechanism 900 may pick each tablet one by one and move them one by one to the measuring device 902. The mechanism 900 may have a picking and holding unit which holds the tablet in the aperture 210 of the wall structure 208 during the measurement. The tablet may move or its movement may be stopped during the measurement. After the measurement, the mechanism 900 may shift the measured tablet back to a feeding system (not shown) for further processing. The mechanism 900 may move the tablets at constant speed and an optical pulse from a transmitter (220 not shown in FIG. 9) such as a laser may be directed at the tablet sample 212 during the time the tablet 212 is in the aperture 210 of the wall structure 208. Although it is possible to stop each tablet 212 for the measurement, inertia of the mechanism 900 would slow down the rate of measurement because of repeated acceleration and deceleration for each tablet 212. Continuous movement may be used to average the variation of the spatial concentration in the tablet 212. The transmission and the reception of the optical radiation may also follow the moving sample 212 during each measurement and then return to a start position for the next measurement. Using this apparatus, it may be possible to make measurements quickly which may enable measurements of all samples of a batch, irrespective of the number of samples in the batch.

If a liquid sample 212 is measured, liquid may be caused to flow in an optically transparent pipe through the aperture 210 in the wall structure 208. Then the feeding mechanism 900 may comprise a pump and the pipe.

Since Raman radiation is effectively collected using the reflecting surface 250, measurements may be performed very quickly. One measurement may take less than one second, even as little as 0.1 second. Because the measurement is so rapid all tablets and capsules produced in a mass production process may be measured. This is an advantage since previously it has been possible only to make a statistical analysis by taking a representative number of tablets from a batch, measuring the tablets, and determining the whole batch as acceptable or not acceptable on basis of the representative measurement.

In the case of a liquid sample, a large volume of liquid may be measured quickly since the speed of flow in the pipe may be high without loss of accuracy in the measurement. This is due to the fact that the liquid cannot flow a long distance between two successive measurements.

In an experiment, an increase by factor of 26× in Raman photons was obtained when a tablet, 5 mm thick, was measured with concave, specular reflecting surfaces 252, 254 on both receiver's and transmitter's side of a wall structure 208 compared to a measurement without the reflecting surfaces 252, 254. This increase in Raman photons in detection enables the achievement of the same signal-to-noise ratio of the measured spectrum much faster than without the reflecting surfaces. Hence, it appears to be possible to make transmission Raman measurements quicker than earlier. The increased speed in measurement may enable 100% inspection of a continuous product. Alternatively, the increased speed in measurement may enable higher accuracy (if integration time of the measurement is kept unchanged) and hence provide fast enough response to allow a use of a closed loop control in the production process.

Figure 10:
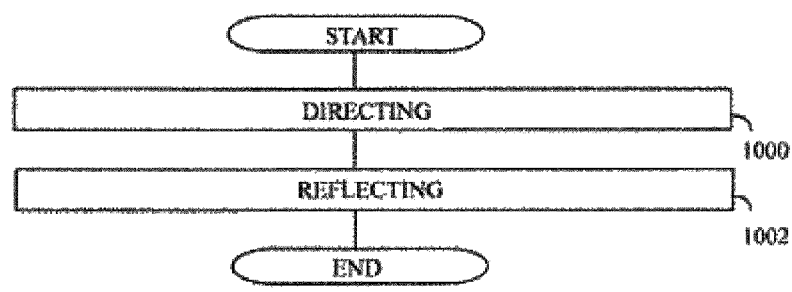
FIG. 10 shows a flow chart of the process of this invention.

FIG. 10 presents a flow chart of the method of the invention. In step 1000, optical excitation radiation is directed to a sample 212 in an optically transparent aperture 210 of a wall structure 208 separating optically a transmitter 220 of the excitation radiation and a receiver 222 during a transmission Raman measurement. In step 1002, optical radiation scattering from the sample 212 is reflected back to the sample 212 by a reflecting surface 250 facing the wall structure 208 for increasing Raman radiation at the receiver 222.

Usually almost or totally white, turbid or diffuse samples are used. On the excitation side, backreflected excitation light (typically 90%) and backreflected Raman signal (both totally diffuse) can be very effectively returned back to the same area which it left by means of the reflecting surface 250. Since the sample is usually at least rather diffuse, the propagation of Raman scattered light on the detection side is diffuse by its nature. This means that at the surface of the sample, i.e. in a layer thickness about 1/scattering constant, the density of Raman scattered photons is much less than somewhat deeper in the sample. This is because the surface of the sample 212 has nothing to reflect or scatter back the photons but instead the photons disappear in the hemispherical space where the pickup probe catches some of them for detection. In this way, the Raman photon density is diluted at the surface of the tablet. However, if a reflecting surface 254 is placed at the detection side, the photons hitting the reflecting surface are returned back to sample 212 and this effect eliminates the dilution process described above. As a result, the intensity of the Raman radiation observed by the pickup probe increases with factor often much larger than 2. The intensity may be increased in a similar manner also on the excitation side which leads to increase in the observed Raman radiation.

Figure 11:
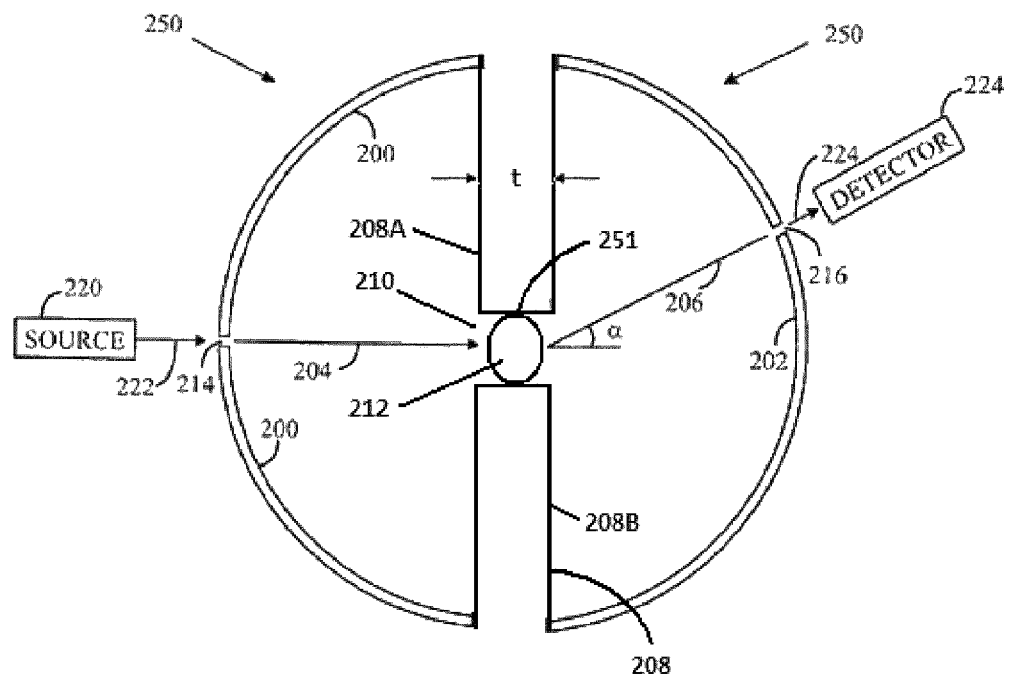
FIG. 11 shows a further construction of reflecting surfaces and wall structure.

FIG. 11 shows an embodiment of the apparatus in which the wall structure 208 has a thickness "t" between its opposed surfaces 208A and 208B on the transmitter 220 and receiver 224 sides. Parts corresponding to earlier Figures are numbered correspondingly. There are two opposite-facing hemispherical reflecting surfaces 250 arranged such that the spherical centre of each hemisphere is at the level of a surface 208A and 208B of the wall structure 208 and the wall structure 208 is across the diameter of the spherical shape formed by the two hemispheres 250. The aperture 210 passes completely through the wall structure 208 from one surface 209A to the other 208B. The thickness "t" is such that the surface of the sample 212 is below one or (as shown) both of the opposite surfaces 208A, 208B of the wall structure 208. The aperture 210 is in effect a tunnel between the two opposite surfaces 208A, 208B of the wall structure 208. The walls 251 of such a tunnel are also specularly reflective. Such a construction facilitates adaptation of the system to samples 212 of different thicknesses in the direction of the thickness of the wall structure 208. Both reflective surfaces 200 are hemispherical reflective surfaces, with their spherical centre at the level of the surfaces 208A, 208B of the wall structure 208.

Although the invention is above described with reference to the examples according to the attached drawings, the invention is not limited thereto. It will be obvious to a person skilled in the art that, as technology advances, the inventive concept can be implemented in various ways. The invention and its embodiments are not limited to the examples described above but may vary within the scope of the claims.

The invention claimed is:

1. An apparatus for measuring Raman radiation scattered from a target sample exposed to excitation radiation, characterised in that the apparatus comprises:
a wall structure optically non-transparent to excitation radiation and having an optically transparent aperture therein, configured to have a sample located within or adjacent to said aperture during measurement of Raman radiation, the wall structure being located between a transmitter of excitation radiation and a receiver for Raman radiation;
an optically reflecting surface, comprising a first hemispherical concave surface and second hemispherical concave surface;
the first concave surface and the second concave surface being configured to face each other with an optical axis between them, and to have a distance of at least their combined hemispherical radii along the optical axes between them;
the wall structure being between the concave surfaces and configured to optically isolate the concave surfaces from each other; the first concave surface comprising an input aperture for transmission of excitation radiation to the sample;
the second concave surface comprising an output aperture for reception of the Raman radiation formed on the interaction between the sample and the excitation radiation on its way through the sample to the receiver, the second concave surface being configured to reflect the optical radiation passed through or reflected from the sample without hitting the output aperture back to the sample;
and the reflecting surface being configured to reflect optical radiation scattered from the sample back to the sample for enhancing Raman radiation at the receiver.

2. The apparatus as claimed in claim 1 characterised in that the transmitter is a laser capable of emitting excitation radiation of wavelength range 700-900 nm.

3. The apparatus as claimed in claim 1 wherein the wall structure is specularly reflective.

4. The apparatus as claimed in claim 1, characterised in that the reflecting surface comprises a first concave surface and second concave reflecting surface one respectively on each side of the wall structure;
the first concave reflecting surface and the second concave reflecting surface are configured to face each other and have a distance of combined focal lengths along the optical axes therebetween;
the wall structure between the concave reflecting surfaces is configured to optically isolate the concave reflecting surfaces from each other;
the first concave reflecting surface comprises an input aperture for transmission of excitation radiation to the sample;
the second concave reflecting surface comprises an output aperture for reception of the Raman radiation formed on the interaction between the sample and the excitation radiation on its way through the sample to the receiver, the second concave reflecting surface being configured to reflect the optical radiation passed through or reflected from the sample without hitting the output aperture back to the sample.

5. The apparatus as claimed in claim 1, characterised in that the optically transparent aperture is configured to be at least approximately at a common focal point of both concave reflecting surfaces.

6. The apparatus as claimed in claim 1, characterised in that there are two hemispherical reflecting surfaces and the wall structure comprises a wall structure across the equatorial diameter each hemispherical reflecting surface such that with a hemispherical reflecting surface on each side of the wall structure, the assembly of reflecting surfaces and wall structure are in the form of a wall across a diameter of a spherical reflecting surface.

7. The apparatus as claimed in claim 1 characterised in that the wall structure has a thickness "t" between its opposed surfaces on the transmitter and receiver sides and the aperture passes completely through the wall structure from one surface to the other, and the thickness "t" is such that the surface of a sample in place in the aperture is below one or both of the opposite surfaces of the wall structure, and the spherical centre of the one or both hemispherical surface(s) is at the level of the surface of the wall structure.

8. The apparatus as claimed in claim 1, characterised in that the optical axis along the excitation beam to the aperture in the wall and the optical axis from the aperture in the wall to the receiver are at an angle to each other of ($\alpha$) the absolute value of the sine function of which is larger than zero but is smaller than one.

9. The apparatus as claimed in claim 8, characterised in that the angle ($\alpha$) is 10-20°.

10. A method of use of an apparatus as claimed in claim 1 in measuring samples on the basis of Raman radiation comprising directing excitation radiation at a sample located within or adjacent to an optically transparent aperture in a wall structure optically non-transparent to the excitation radiation, the wall structure being located between a transmitter of excitation radiation and a receiver for Raman radiation;

and reflecting scattered radiation from the sample back to the sample from a reflecting surface facing the wall structure for enhancing Raman radiation at the receiver.

11. The method as claimed in claim 10 characterised in that the sample is a pharmaceutical tablet.

\* \* \* \* \*